United States Patent [19]

Döller et al.

[11] Patent Number: 5,608,062

[45] Date of Patent: Mar. 4, 1997

[54] PROCESS FOR PREPARING TRIFLUOROMETHYL KETONES

[75] Inventors: Uwe Döller, Rodgau; Bernd Scharbert, Frankfurt; Laurent Weisse, Oberursel, all of Germany

[73] Assignee: Hoechst Schering AgrEvo GmbH, Berlin, Germany

[21] Appl. No.: 256,523

[22] PCT Filed: Jan. 15, 1993

[86] PCT No.: PCT/EP93/00094

§ 371 Date: Sep. 21, 1994

§ 102(e) Date: Sep. 21, 1994

[87] PCT Pub. No.: WO93/14054

PCT Pub. Date: Jul. 22, 1993

[30] Foreign Application Priority Data

Jan. 21, 1992 [DE] Germany ............ 42 01 435.2

[51] Int. Cl.$^6$ ............ C07D 233/22; C07D 213/50; C07D 239/36; C07D 277/34
[52] U.S. Cl. ............ 544/238; 544/335; 546/298; 546/314; 546/315; 548/200; 548/333.5; 549/70
[58] Field of Search ............ 568/335, 337, 568/403; 546/298, 314, 315; 549/70; 544/238, 335; 548/200, 333.5

[56] References Cited

U.S. PATENT DOCUMENTS 3,996,259  12/1976  Lee et al. ............ 558/308

OTHER PUBLICATIONS

Linderman, Russell J., et al., "An Efficient Procedure for the Oxidation of Fluorinated Carbinols", *Tetrahedron Letters* 28(37): 4259–4262 (1987).

Jean–Pierre Bégué and Danièle Bonnet-Delpon, Tetrahedron Report No. 290, "Preparation of Trifluoromethyl Ketones and Related Fluorinated Ketones", *Tetrahedron* vol. 47, No. 20/21, pp. 3207–3258, 1991.

*Primary Examiner*—Alan L. Rotman
*Attorney, Agent, or Firm*—Curtis, Morris & Safford, P.C.

[57] ABSTRACT

A process is described for preparing trifluoromethyl ketones of the formula I

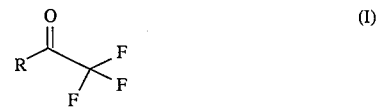

where R has the given meanings, wherein an alcohol of the formula II

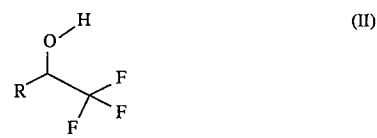

is reacted with a compound of the formula IV $$YO_nH \qquad (IV)$$

where n has the given meaning.

11 Claims, No Drawings

PROCESS FOR PREPARING TRIFLUOROMETHYL KETONES

CROSS-REFERENCE

This application is a 371 of PCT/EP 93/00094 filed Jan. 15, 1993.

DESCRIPTION

The present invention relates to a process for preparing trifluoromethyl ketones of the formula I

where R is an unsubstituted or substituted aliphatic or aromatic hydrocarbon radical or an unsubstituted or substituted aliphatic or aromatic heterocyclic radical, wherein an alcohol of the formula II

where R has the abovementioned meaning, is reacted in an aprotic solvent, preferably methylene chloride, chloroform, ethyl acetate, toluene, xylene or chlorobenzene, in the presence of 0.1–20 mol %, preferably of 1–10 mol %, based on the alcohol of the structure II employed, of a phase-transfer catalyst, with a 1–20% strength by weight aqueous solution of a compound of the structure IV or a 1–20% strength by weight aqueous solution of a compound generated in situ of the structure IV

$$YO_nH \qquad (IV)$$

where Y is =Cl, Br or I and n is =an integer from 1 to 4, or of its salts, at temperatures from 0° C. up to the boiling point of the mixture.

The compounds of the formula I are important starting products and intermediates in the synthesis, for example, of pharmaceuticals, plant protection agents (EP-A-0386 715), plastics (U.S. Pat. No. 3,342,778), surface-active substances (DD 2397 88 A1), materials for non-linear optics (WO 91/08198), liquid crystals and dyes.

It is known that trifluoromethyl alcohols are inert towards a multiplicity of oxidizing agents (Tetrahedron (1991), 47 (20/21), 3207).

Reactions of alcohols of the structure II with dimethyl sulfoxide at −55° C. in the presence of oxalyl chloride (AU-B-52 881/86) to form the ketones I require more than 3 mol of the oxidizing agent per mol of the alcohols II employed. The procedure for the reaction must be seen as being disadvantageous for the industrial scale. The use of large quantities of oxalyl chloride is unacceptable for economic reasons. The dimethyl sulfide arising during the reaction must be considered disadvantageous from the ecological point of view.

The preparation of trifluoromethyl ketones of the structure I by oxidation of alcohols of the formula II using the Dess-Martin reagent (J. Org. Chem. (1989), 54, 661) requires the use of expensive, hypervalent iodine compounds which are hazardous and are not available commercially. In particular, the industrial use of Dess-Martin reagent is to be considered disadvantageous from the economic and safety points of view.

The use of alkaline permanganate solution (Tetrahedron Lett. (1986), 27 (2), 135) for the oxidation of compounds of the structure II is limited to water-soluble trifluoromethyl alcohols and gives results which are not very reproducible (J. Org. Chem. 1989, 54, 661).

The use of chromic acids for synthesizing the type I compounds from the alcohols II (J. Org. Chem. (1968), 33 (3), 1016) requires drastic reaction conditions and reaction times of several days, and can therefore be used to advantage only for inert, perhalogenated alcohols. The resulting chromium salt waste must be considered disadvantageous from the economic and ecological points of view.

All these disadvantages which have been described are avoided by the process according to the invention, which is very simple to perform and which is also suitable for continuous operation. Under the conditions according to the invention, the products I can be obtained in high yields, e.g. up to 90% of theory, and at high purity, using readily available, economically advantageous oxidizing agents of the structure IV. At the same time the radical R can be varied very widely.

When in the form of a hydrocarbon radical, R in formula I contains preferably 1 to 30, particularly 1 to 20 and in particular 1 to 12 carbon atoms, and when in the form of a heterocyclic radical, R contains preferably 1 to 4 hetero atoms in the ring. The ring contains preferably 4 to 8, particularly 5 or 6 ring members. The hetero atoms are preferably O, S or N and identical or different hetero atoms may be contained within the ring.

R in the form of an aliphatic hydrocarbon radical is preferably unsubstituted or substituted alkyl, alkenyl, alkynyl, cycloalkyl or cycloalkenyl, in the form of an unsubstituted or substituted aromatic hydrocarbon radical is aryl, aralkenyl, aralkynyl or aralkyl, in the form of an unsubstituted or substituted aliphatic heterocyclic radical is a 3- to 7-membered heterocyclic ring containing 1 to 3 hetero atoms, and in the form of an aromatic heterocyclic radical is a 5- or 6-membered heterocyclic ring containing 1 to 4 hetero atoms.

Examples of alkyl are methyl, ethyl, n-propyl, isopropyl, n-, iso- and tertiary-butyl, pentyl, hexyl, octyl, 2-ethylhexyl, nonyl, decyl, undecyl, dodecyl, tetradecyl, octadecyl and eicosyl.

Examples of alkenyl are vinyl, allyl, 1- or 2-methylvinyl, styryl, butenyl, pentenyl, hexenyl, octenyl, decenyl and dodecenyl.

Examples of alkynyl eare ethynyl, propargyl, methylethynyl, phenylethynyl, butynyl, pentynyl, hexynyl, octynyl, decynyl and dodecynyl.

The cycloalkyl and cycloalkenyl can contain 3 to 12, preferably 3 to 8 and in particular 3 to 6 carbon atoms in the ring. Examples are cyclopropyl, cyclobutyl, cyclopentyl, cyclohexyl, cycloheptyl, cyclooctyl, cyclononyl, cyclodecyl, cyclododecyl, cyclopropenyl, cyclobutenyl, cyclopentadienyl, cyclohexenyl, cyclohexadienyl, cyclooctenyl, cyclooctadienyl, bicyclo-2.2.2-octenyl, bicyclo-2.2.1-heptenyl.

The aromatic hydrocarbon radical can be mononuclear or polynuclear, preferably monocyclic or bicyclic, and can be condensed. Preferred radicals are aryl, aralkenyl, aralkynyl or aralkyl with in particular 6 to 18 or 7 to 18 or 8 to 18 carbon atoms, respectively. The aryl is preferably phenyl or naphthyl. Examples are phenyl, naphthyl, benzyl, phenylethyl, 2-phenylpropyl, naphthylmethyl, dihydronaphthalene, indan, indene, fluorene and phenanthrene.

In the form of an aliphatic heterocyclic radical, R has preferably 4 to 6 ring members and comprises, depending on ring size, 1 to 3, preferably 1 or 2, hetero atoms such as O, S or N. Examples of heterocyclic rings from which the radical R is derived are: oxetane, oxolane, oxolene, oxane, dioxane, aziridine, azetidine, azetine, pyrrolidine, pyrroline, tetrahydrothiophene, 2,3-dihydroindole, dihydrocoumarone, dihydrothionaphthene, pyrazolidine, imidazolidine, oxazolidine, thiazolidine, triazolidine, oxadiazolidine, morpholine, piperidine, tetrahydroquinoline.

In the form of an aromatic heterocyclic radical, R contains preferably 1 to 4, particular 1 to 2, hetero atoms such as O, S and N, and is preferably a 5- or 6-membered ring. In addition, condensed ring systems are also possible. Examples of heteroaromatics from which R can be derived are: pyrrole, furan, thiophene, pyridine, pyran, pyrazole, imidazole, benzimidazole, triazine, oxazole, thiazole, pyridazine, pyrimidine, pyrazine, quinoline, isoquinoline, chromene, purine, xanthene and indole.

The R radicals are unsubstituted or substituted one or more times, in particular 1 to 5 times. The number of substituents depends, inter alia, on the size of the aromatic systems. In the case of multiple substitution, the substituents are identical or different. The substituents may themselves be substituted.

Radicals which are not attacked under the reaction conditions are suitable substituents for the radical R.

Suitable substituents for R are, for example: $C_1$–$C_{18}$-alkyl, $C_2$–$C_{18}$-alkenyl, $C_2$–$C_{18}$-alkynyl, $C_6$–$C_{18}$-aryl, $C_7$–$C_{18}$-aralkyl, $C_7$–$C_{18}$-alkaryl, $C_8$–$C_{18}$-alkarylalkyl, $C_1$–$C_{18}$-alkoxy, $C_1$–$C_{18}$-alkylthio, $C_6$–$C_{18}$-aryloxy, $C_7$–$C_{18}$-aralkoxy, $C_7$–$C_{18}$-aralkylthio, $C_7$–$C_{18}$-alkaryloxy, $C_8$–$C_{18}$-alkaralkoxy, $C_7$–$C_{18}$-aryloxyalkyl, $C_7$–$C_{18}$-alkoxyaryl, hetaryl, hetarylalkyl, alkylhetaryl, alkylhetarylalkyl, hetaryloxy, hetarylalkyloxy, hetarylalkylthio, alkylhetaryloxy, alkoxyhetaryl, alkylhetarylalkyloxy, hetaryloxyalkyl, the heterocyclic aryl radicals each having up to 8 carbon atoms and up to 4 hetero atoms, selected from the group comprising N, S and O, and the alkyl groups which may be present possessing in all up to 12 carbon atoms, $C_3$–$C_{12}$-cycloalkyl, $C_3$–$C_{12}$-cycloalkoxy, $C_3$–$C_{12}$-cycloalkenyl, $C_3$–$C_{12}$-cycloalkenyloxy, $C_1$–$C_{18}$-haloalkyl, in particular fluoroalkyl, —CN, OH, $NO_2$, F, Cl, Br, I, —NCO, $COOR^1$, $COR^1$, $OCOR^1$, $CONR^1R^2$, $NR^1COR^2$, $NR^1R^2$, $SO_2NR^1R^2$, $Si(R^1)_3$, $SO_2R^1$, $SO_3R^1$, $PO_2R^1$ and $PO_3R^1R^2$. In the above-listed substituents, $R^1$ is H, $C_1$–$C_{18}$-alkyl, $C_1$–$C_{18}$-haloalkyl, in particular $C_1$–$C_{18}$-fluoroalkyl, $C_3$–$C_6$-cycloalkyl, phenyl, benzyl or pyridyl; $R^2$ has independently the same meaning as $R^1$.

The aliphatic R radicals can be interrupted by O, S, $NR^1$, where $R^1$ has the meaning indicated above, —CO— or —C(O)O—.

Aryl as substituent for R is preferably phenyl or naphthyl, and hetaryl is preferably pyridyl, pyrimidyl or pyridazinyl, thiazolyl or imidazolyl. Preferred substituents of the named aromatic radicals are $C_1$–$C_{12}$-alkyl, phenyl, benzyl, $C_7$–$C_{14}$-alkylphenyl, $C_8$–$C_{14}$-alkylbenzyl, $C_1$–$C_{12}$-alkoxy, phenoxy, benzyloxy, $C_7$–$C_{12}$-alkylphenoxy, $C_8$–$C_4$-alkylbenzyloxy, $C_7$–$C_{12}$-phenoxyalkyl, $C_7$–$C_{14}$-alkoxyphenyl, cyclopentyl, cyclohexyl, cyclopropyl, $C_1$–$C_{12}$-haloalkyl, in particular $C_1$–$C_{12}$-fluoroalkyl, $C_1$–$C_{12}$-haloalkoxy, in particular $C_1$–$C_{12}$-fluoroalkoxy, CN, OH, F, Cl, Br, I, where the aliphatic radicals may be interrupted as previously defined.

Some examples of substituents on the R radical are: methyl, ethyl, propyl, butyl, vinyl, allyl, ethynyl, propargyl, phenyl, benzyl, methylbenzyl, methylphenyl, methoxy, ethoxy, propoxy, butoxy, methylthio, phenoxy, benzyloxy, methylphenoxy, methylbenzyloxy, phenoxymethyl, methoxyphenoxy, cyclopentyl, cyclohexyl, cyclohexenyl, cyclohexyloxy, methoxycarbonyl, methylamino, dimethylamino, methylaminocarbonyl, alkoxyalkyl such as methoxymethyl or methoxyethyl, alkylaminoalkyl such as methylaminomethyl or dimethylaminoethyl, phenoxyphenyl, methoxycarbonylmethyl, ethoxycarbonylethyl, haloalkyl such as chloromethyl, dichloromethyl, trichloromethyl, fluoromethyl, difluoromethyl, trichloroethyl, trifluoromethyl, hexafluoropropyl, trifluoroethyl, haloalkoxy such as monofluoromethoxy, difluoromethoxy, trifluoromethoxy, trifluoroethoxy, trichloroethoxy or hexafluoropropoxy, haloaryl such as fluorophenyl, chlorophenyl, haloaryloxy such as fluorophenoxy, chlorophenoxy, haloalkoxyaryl such as trifluoromethoxyphenyl, trifluoroethoxyphenyl as well as trifluoromethylphenyl, trifluoromethylphenoxy and trifluoroethoxypyridyl.

In a preferred subgroup, R is $C_1$–$C_6$-alkyl, $C_3$–$C_6$-cycloalkyl, $C_1$–$C_6$-haloalkyl or unsubstituted or substituted phenyl, benzyl, pyridyl, pyrimidyl, pyridazinyl or thiazolyl, with halogen, $C_1$–$C_6$-haloalkyl, $C_1$–$C_6$-haloalkoxy, $C_1$–$C_6$-alkyl and $C_1$–$C_6$-alkoxy being suitable substituents.

In the preceding and subsequent text, alkyl, alkenyl, alkynyl and alkoxy are understood as meaning linear and branched-chain groups, unless otherwise indicated.

Suitable phase-transfer catalysts are, for example, polyethers, preferably polyethylene glycols, phosphonium salts and in particular ammonium salts of the formula III

where $R^3$–$R^6$ are the same or different and are benzyl, phenyl, $(C_1$–$C_{16})$-alkyl, preferably $(C_1$–$C_8)$-alkyl, in particular butyl, and $X^-$ is $OH^-$ or anions of monobasic or polybasic acids, in particular $Cl^-$, $Br^-$ or $HSO_4^-$.

The following compounds of the structure III, which are to be used according to the invention and where $R^3$–$R^6$ and $X^-$ have the abovementioned meaning, may be mentioned by way of example: benzyltrimethylammonium chloride, tetraethylammonium bromide, tetrapropylammonium bromide, hexadecyltrimethylammonium bromide, benzyltributylammonium chloride, preferably tetrabutylammonium bromide or tetrabutylammonium hydrogen sulfate.

Under the conditions according to the invention, the compounds of structure III are added at 0.1–20 mol %, in relation to the compounds of structure II employed, preferably, however, at 1–10 mol %.

The compounds of structure IV are used as such or in the form of their salts, in particular the alkali metal salts or alkaline earth metal salts. Preferred compounds IV are HOCl, $HClO_4$, HOBr, $HBrO_2$, $HBrO_3$, $HIO_4$ and their salts, in particular HOCl, HOBr and their alkali metal salts or alkaline earth metal salts. In particular, sodium, potassium and calcium salts are suitable, for example sodium hyochlorite, potassium hyochlorite, sodium perchlorate, sodium hyobromite, sodium bromate, sodium bromite, calcium hyochlorite, preferably, however, sodium hypochlorite, sodium hypobromite and calcium hypochlorite.

The compounds of the formula IV are generally known oxidizing agents and can be employed as such in the process according to the invention or be generated in situ by suitable methods. Suitable methods are, for example, generation by electrochemical means (J. Appl. Electrochem. (1989), 19, 922) or the reaction of $H_2O_2$ with hydrohalic acids or their salts in an aqueous medium (DE-A-21 10 210).

The use of compounds of the structure IV in the form of their aqueous solutions is preferred.

Electrochemical generation is preferred for generating the oxidizing agents of the structure IV in situ.

The content of IV is 1–20% by weight, preferably 5–15% by weight. For in situ generation, it is not necessary to determine the concentration of the compounds of the structure IV, since the compounds of the structure IV are generated in the presence of the compounds of the structure II and are removed by reaction with the latter.

The quantity of oxidizing agent IV which is needed for preparing the compound of the formula I is at least 1 mol per mol of starting material II, preferably 1–4 mol per mol of starting material II, in particular 1–2 mol per mol of alcohol II.

The reaction according to the invention of the compounds II and IV in the presence of a phase-transfer catalyst, such as, for example, a compound III, is effected in a two-phase system at temperatures from 0° C. up to the boiling point of the mixture.

The reaction according to the invention of the compounds II and IV in the presence of III is preferably effected in the temperature range from 0° to 40° C.

The process according to the invention can expediently be carried out by taking a solution of an alcohol of the structure II at room temperature and, in the presence of a phase-transfer catalyst of the structure III, either metering in an aqueous solution of the oxidizing agent of the structure IV while stirring vigorously, or else generating the latter in aqueous solution in situ. After reacting for up to a further 8 hours, the phases are separated and the aqueous phase is extracted several times. The combined organic phases are washed with saturated, aqueous sodium chloride solution, the organic phase is dried with sodium sulfate and the volatiles are distilled off. The remaining crude product is purified by distillation under high vacuum. The ketones of the structure I are obtained in high purity.

The in situ electrochemical generation of the oxidizing agent is state of the art [J. Appl. Electrochem. 19 (1989) 922]. It is carried out by means of a galvanostat in an undivided cell on inert electrodes. In the electrolysis cell there is an aqueous solution of a compound YH, where Y has the abovementioned meaning, or of its salts, at a concentration of 0.001–2 mol/l, preferably of 0.05 to 0.5 mol/l, as well as the aprotic solvent together with the phase-transfer catalyst, preferably with the structure III, and the compound of the structure II, as described.

The pH of the aqueous solution during the electrolysis is in the range from 5 to 11, preferably from 6.5 to 10.5. The current density is kept in the range from 1 to 100 mA/cm$^2$, preferably from 10 to 40 mA/cm$^2$. The current flow is in the range from 1 to 20 F/mol, preferably from 2 to 10 F/mol.

The compounds of the formula II, where R has the above-mentioned meaning, can be obtained from the corresponding aldehydes and trifluorobromomethane in the presence of zinc (U.S. Pat. No. 4,701,569).

The following examples serve to illustrate the invention in more detail:

EXAMPLE 1

2-Chloro-5-trifluoroacetylpyridine 21.13 g (0.1 mol) of 2-chloro-5-(2,2,2-trifluoro-1-hydroxyethyl)pyridine and 1.8 g (0.005 mol) of tetrabutylammonium hydrogen sulfate are dissolved in 200 ml of ethyl acetate at room temperature. 61 ml (0.12 mol) of an approximately 12% strength sodium hypochlorite solution are metered in within 15 minutes with vigorous stirring and the mixture is stirred for a further 2 hours during which the reaction temperature rises to 40° C. The phases are separated, the aqueous phase is extracted several times with ethyl acetate and the combined organic phases are washed with saturated aqueous sodium chloride solution. After drying the organic phase with sodium sulfate, the volatiles are distilled off. Following distillation of the crude product at 0.3 mbar, 15.6 g (74.4% of theory) of 2-chloro-5-trifluoroacetylpyridine with a boiling point of 50°–51° C. are obtained, which, according to GC, is 99.8% pure. $n_D^{20}$: 1.4887.

EXAMPLE 2

2-Chloro-5-trifluoroacetylpyridine 2.11 g (0.01 mol) of 2-chloro-5-(2,2,2-trifluoro-1-hydroxyethyl)pyridine and 0.18 g (0.0005 mol) of tetrabutylammonium hydrogen sulfate are dissolved in 30 ml of methylene chloride at room temperature. 7.3 ml (0.012 mol) of an approximately 10% strength sodium hypochlorite solution are metered in within 5 minutes with vigorous stirring and the mixture is stirred for a further 2 hours during which the reaction temperature rises to 30° C. The reaction mixture is added to 50 ml of water, the phases are separated, the aqueous phase is extracted several times with methylene chloride and the combined organic phases are washed with saturated aqueous sodium sodium chloride solution. After drying the organic phase with sodium sulfate, the volatiles are distilled off. Following distillation of the crude product in a kugelrohr (0.5 mbar, 100°–120° C. bath temperature), 1.13 g (54% of theory) of 2-chloro-5-trifluoroacetylpyridine are obtained, which, according to GC, is 99.8% pure. $n_D^{20}$: 1.4887.

EXAMPLE 3

2-Chloro-5-trifluoroacetylpyridine 2.11 g (0.01 mol) of 2-chloro-5-(2,2,2-trifluoro- 1-hydroxyethyl)pyridine and 0.18 g (0.0005 mol) of tetrabutylammonium hydrogen sulfate are dissolved in 25 ml of chlorobenzene at room temperature. 12 ml (0.02 mol) of an approximately 12% strength sodium hypochlorite solution are metered in within 10 minutes with vigorous stirring and the mixture is stirred for a further 4 hours during which the reaction temperature rises to 30° C. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.5 mbar, 100°–120° C. bath temperature), 1.41 g (67% of theory) of 2-chloro-5-trifluoroacetylpyridine are obtained, which, according to GC, is 98% pure.

EXAMPLE 4

2-Chloro-5-trifluoroacetylpyridine 2.11 g (0.01 mol) of 2-chloro-5-(2,2,2-trifluoro-1-hydroxyethyl)pyridine and 0.18 g (0.0005 mol) of tetrabutylammonium hydrogen sulfate are dissolved in 30 ml of xylene at room temperature. 7.3 ml (0.012 mol) of an approximately 10% strength sodium hypochlorite solution are metered in within 5 minutes with vigorous stirring and the mixture is stirred for a further 2 hours during which the reaction temperature rises to 28° C. The reaction mixture is added to 50 ml of water, the phases are separated, the aqueous phase is extracted several times with xylene and the combined organic phases are washed with saturated aqueous sodium chloride solution. After drying the organic phase with sodium sulfate, the volatiles are distilled off. Following distillation of the crude product in a kugelrohr (0.4 mbar, 100°–110° C. bath temperature), 1.89 g (90% of theory) of 2-chloro-5-trifluoroacetylpyridine are obtained.

EXAMPLE 5

2-Chloro-5-trifluoroacetylpyridine 2.11 g (0.01 mol) of 2-chloro-5-(2,2,2-trifluoro-1-hydroxyethyl)pyridine and 0.18 g (0.0005 mol) of tetrabutylammnonium hydrogen sulfate are dissolved in 25 ml of toluene at room temperature. 6.1 ml (0.012 mol) of an approximately 12% strength sodium hypochlorite solution are metered in within 5 minutes with vigorous stirring and the mixture is stirred for a further 2.5 hours during which the reaction temperature rises to 27° C. The reaction mixture is added to 50 ml of water, the phases are separated, the aqueous phase is extracted several times with toluene and the combined organic phases are washed with saturated aqueous sodium chloride solution. After drying the organic phases with sodium sulfate, the volatiles are distilled off. Following distillation of the crude product in a kugelrohr (0.4 mbar, 100°–115° C. bath temperature), 1.78 g (85% of theory) of 2-chloro- 5-trifluoroacetylpyridine are obtained.

EXAMPLE 6

2-Chloro-5-trifluoroacetylpyridine 2.11 g (0.01 mol) of 2-chloro-5-(2,2,2-trifluoro-1-hydroxyethyl)pyridine and 0.17 g (0.0005 mol) of tetrabutylammonium bromide are dissolved in 25 ml of methylene chloride at room temperature. 12 ml (0.02 mol) of an approximately 12% strength sodium hypochlorite solution are metered in within 5 minutes, with vigorous stirring and the mixture is stirred for a further 4 hours during which the reaction temperature rises to 30° C. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.5 mbar, 100°–120° C. bath temperature), 1.47 g (70.5% of theory) of 2-chloro-5-trifluoroacetylpyridine are obtained.

EXAMPLE 7

2-Chloro-5-trifluoroacetylpyridine 2.11 g (0.01 mol) of 2-chloro-5-(2,2,2-trifluoro-1-hydroxyethyl)pyridine and 0.18 g (0.0005 mol) of tetrabutylammonium hydrogen sulfate are dissolved in 20 ml of methylene chloride at room temperature. After addition of 4 ml of water and 1.72 g (0.012 mol) of calcium hypochlorite the mixture is stirred for 2.25 hours with vigorous mixing, during which the reaction temperature rises to 28° C. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.4 mbar, 100°–110° C. bath temperature), 1.69 g (81% of theory) of 2-chloro-5-trifluoroacetylpyridine are obtained.

EXAMPLE 8

2-(2,2,2-Trifluoroethoxy)-5-trifluoroacetylpyridine 2.75 g (0.01 mol) of 2-(2,2,2-trifluoroethoxy)-5-(2,2,2-trifluoro-1-hydroxyethyl)pyridine and 0.18 g (0.0005 mol) of tetrabutylammonium hydrogen sulfate are dissolved in 30 ml of methylene chloride at room temperature. 22 ml (0.036 mol) of an approximately 12% strength sodium hypochlorite solution are metered in within 10 minutes with vigorous stirring and the mixture is stirred for a further 4.5 hours during which the reaction temperature rises to 25° C. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.3 mbar, 100°–120° C. bath temperature), 2.48 g (90% of theory) of 2-(2,2,2-trifluoroethoxy)-5-trifluoroacetylpyridine are obtained, which, according to GC, is 96% pure. $n_D^{20}$: 1.4312.

EXAMPLE 9

2-(2,2,2-Trifluoroethoxy)-5-trifluoroacetylpyridine 43.15 g (0.157 mol) of 2-(2,2,2-trifluoroethoxy)-5-(2,2,2-trifluoro-1-hydroxyethyl)pyridine and 2.66 g (0.0078 mol) of tetrabutylammonium hydrogen sulfate are dissolved in 400 ml of ethyl acetate at room temperature. 240 ml (0.235 mol) of an approximately 6% strength sodium hypochlorite solution are metered in within 1 hour with vigorous stirring and the mixture is stirred for a further 2 hours during which the reaction temperature rises to 40° C. The reaction mixture is added to 500 ml of water, the phases are separated, the aqueous phase is extracted several times with ethyl acetate and the combined organic phases are washed with saturated aqueous sodium chloride solution. After drying the organic phase with sodium sulfate, the volatiles are distilled off. Following distillation of the crude product (27 torr, 100°–102° C.), 24.47 g (57% of theory) of 2-(2,2,2-trifluoroethoxy)-5-trifluoroacetylpyridine are obtained, which, according to GC, is 97% pure.

EXAMPLE 10

2-(2,2,2-Trifluoroethoxy)-5-trifluoroacetylpyridine 2.75g (0.01 mol) of 2-(2,2,2-trifluoroethoxy)-5-(2,2,2-trifluoro-1-hydroxyethyl)pyridine and 0.18 g (0.0005 mol) of tetrabutylammonium hydrogen sulfate are dissolved in 25 ml of chlorobenzene at room temperature. 12.2 ml (0.012 mol) of an approximately 6% strength sodium hypochlorite solution are metered in within 10 minutes with vigorous stirring and the mixture is stirred for a further 8 hours during which the reaction temperature rises to 24° C. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled

EXAMPLE 11

2-(2,2,2-Trifluoroethoxy)-5-trifluoroacetylpyridine 2.75 g (0.01 mol) of 2-(2,2,2-trifluoroethoxy)-5-(2,2,2-trifluoro-1-hydroxyethyl)pyridine and 0.18 g (0.0005 mol) of tetrabutylammonium hydrogen sulfate are dissolved in 30 ml of xylene at room temperature. 6.1 ml (0.012 mol) of an approximately 12% strength sodium hypochlorite solution are metered in within 5 minutes with vigorous stirring and the mixture is stirred for a further 4 hours during which the reaction temperature rises to 28° C. The reaction mixture is added to 50 ml of water, the phases are separated, the aqueous phase is extracted several times with xylene and the combined organic phases are washed with saturated aqueous sodium chloride solution. After drying the organic phase with sodium sulfate, the volatiles are distilled off. Following distillation of the crude product in a kugelrohr (0.3 mbar, 100°–125° C. bath temperature), 2.31 g (84.7% of theory) of 2-(2,2,2-trifluoroethoxy)-5-trifluoroacetylpyridine are obtained.

EXAMPLE 12

2-(2,2,2-Trifluoroethoxy)-5-trifluoroacetylpyridine 2.75 g (0.01 mol) of 2-(2,2,2-trifluoroethoxy)-5-(2,2,2-trifluoro-1-hydroxyethyl)pyridine and 0.18 g (0.0005 mol) of tetrabutylammonium hydrogen sulfate are dissolved in 20 ml of methylene chloride at room temperature. After addition of 4 ml of water and 1.72 g (0.012 mol) of calcium hypochlorite the mixture is stirred for 4 hours with vigorous mixing, during which the reaction temperature rises to 25° C. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.3 mbar, 100°–120° C. bath temperature), 2.38 g (87% of theory) of 2-(2,2,2-trifluoroethoxy)-5-trifluoroacetylpyridine are obtained.

EXAMPLE 13

2-(2,2,2-Trifluoroethoxy)-5-trifluoroacetylpyridine 2.75 g (0.01 mol) of 2-(2,2,2-trifluoroethoxy)-5-(2,2,2-trifluoro-1-hydroxyethyl)-pyridine and 0.17 g (0.0005 mol) of tetrabutylammonium bromide are dissolved in 25 ml of methylene chloride at room temperature. 12.2 ml (0.012 mol) of an approximately 6% strength sodium hypochlorite solution are metered in within 10 minutes with vigorous stirring and the mixture is stirred for a further 8 hours during which the reaction temperature rises to 27° C. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.3 mbar, 100°–120° C. bath temperature), 1.31 g (48% of theory) of 2-(2,2,2-trifluoroethoxy)-5-trifluoroacetylpyridine are obtained.

EXAMPLE 14

2-(2,2,2-Trifluoroethoxy)-5-trifluoroacetylpyridine 2.75 g (0.01 mol) of 2-(2,2,2-trifluoroethoxy)-5-(2,2,2-trifluoro-1-hydroxyethyl)pyridine and 0.17 g (0.0005 mol) of tetrabutylammonium bromide are dissolved in 30 ml of chlorobenzene at room temperature. 6.1 ml (0.012 mol) of an approximately 12% strength sodium hypochlorite solution are metered in within 5 minutes with vigorous stirring and the mixture is stirred for a further 4 hours at room temperature. The reaction mixture is added to 50 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.3 mbar, 100°–120° C. bath temperature), 0.68 g (24.7% of theory) of 2-(2,2,2-trifluoroethoxy)- 5-trifluoroacetylpyridine are obtained.

EXAMPLE 15

4-Trifluoroacetylbromobenzene 6.88 g (0.027 mol) of 2,2,2-trifluoro-1-(4-bromophenyl)ethanol and 0.46 g (0.00135 mol) of tetrabutylammonium hydrogen sulfate are dissolved in 100 ml of methylene chloride at room temperature. 16.6 ml (0.032 mol) of an approximately 12% strength sodium hypochlorite solution are metered in within 15 minutes with vigorous stirring and the mixture is stirred for a further 6 hours during which the reaction temperature rises to 28° C. The reaction mixture is added to 100 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.5 mbar, 90°–110° C. bath temperature), 4.13 g (60.4% of theory) of 4-trifluoroacetylbromobenzene are obtained. $n_D^{20}$: 1.5112.

EXAMPLE 16

3-Trifluoroacetyldiphenyl ether 3.34 g (0.0125 mol) of 2,2,2-trifluoro-1-(3-phenoxphenyl)ethanol and 0.21 g (0.0006 mol) of tetrabutylammonium hydrogen sulfate are dissolved in 75 ml of methylene chloride at room temperature. 7.7 ml (0.015 mol) of an approximately 12% strength sodium hyochlorite solution are metered in within 10 minutes with vigorous stirring and the mixture is stirred for a further 6 hours during which the reaction temperature rises to 27° C. The reaction mixture is added to 100 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.5 mbar, 150°–180° C. bath temperature), 2.09 g (62.7% of theory) of 3-trifluoroacetyldiphenyl ether are obtained. $n_D^{20}$: 1.5348.

EXAMPLE 17

3-Trifluoroacetylanisole 4.82 g (0.023 mol) of 2,2,2-trifluoro-1-(3-methoxyphenyl)ethanol and 0.4 g (0.0012 mol) of tetrabutylammonium hydrogen sulfate are dissolved in 100 ml of methylene chloride at room temperature. 14.4 ml (0.028 mol) of an approximately 12% strength sodium hypochlorite solution are metered in within 15 minutes with vigorous stirring and the mixture is stirred for a further 6 hours during which the reaction temperature rises to 26° C. The reaction mixture is added to 100 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.2 mbar, 60°–70° C. bath temperature), 2.1 g (44% of theory) of 3-trifluoroacetylanisole are obtained. $n_D^{20}$: 1.4773.

EXAMPLE 18

2-Bromo-4-trifluoroacetylfluorobenzene 6.4 g (0.023 mol) of 2,2,2-trifluoro-1-(3-bromo-4-fluorophenyl)ethanol and 0.4 g (0.0012 mol) of tetrabutylammonium hydrogen sulfate are dissolved in 100 ml of methylene chloride at room temperature. 14.4 ml (0.028 mol) of an approximately 12% strength sodium hypochlorite solution are metered in within 15 minutes with vigorous stirring and the mixture is stirred for a further 4 hours during which the reaction temperature rises to 27° C. The reaction mixture is added to 100 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.5 mbar, 80°–100° C. bath temperature), 3.9 g (61.5% of theory) of 2-bromo-4-trifluoroacetylfluorobenzene are obtained. $n_D^{20}$: 1.4905.

EXAMPLE 19

4-Trifluoroacetyltoluene 2.88 g (0.015 mol) of 2,2,2-trifluoro-1-(4-methylphenyl)ethanol and 0.26 g (0.0007 mol) of tetrabutylammonium hydrogen sulfate are dissolved in 125 ml of methylene chloride at room temperature. 9.3 ml (0.018 mol) of an approximately 12% strength sodium hypochlorite solution are metered in within 10 minutes with vigorous stirring and the mixture is stirred for a further 4 hours at room temperature. The reaction mixture is added to 100 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.4 mbar, 60°–70° C. bath temperature), 0.84 g (30% of theory) of 4-trifluoroacetyltoluene are obtained. $n_D^{20}$: 1.4675.

EXAMPLE 20

5-Bromo-2-trifluoroacetylthiophene 2.93 g (0.011 mol) of 2,2,2-trifluoro-1-(5-bromo-2-thienyl)ethanol and 0.19 g (0.0006 mol) of tetrabutylammonium hydrogen sulfate are dissolved in 100 ml of methylene chloride at room temperature. 6.9 ml (0.014 mol) of an approximately 12% strength sodium hyochlorite solution are metered in within 5 minutes with vigorous stirring and the mixture is stirred for a further 4 hours at room temperature. The reaction mixture is added to 100 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.3 mbar, 40°–60° C. bath temperature), 0.48 g (39% of theory) of 5-bromo-2-trifluoroacetylthiophene. $n_D^{20}$: 1.5309.

EXAMPLE 21

3-Trifluoroacetylpyridine 13.2 g (0.075 mol) of 2,2,2-trifluoro-1-(3-pyridyl)ethanol and 1.26 g (0.0037 mol) of tetrabutylammonium hydrogen sulfate are dissolved in 250 ml of methylene chloride at room temperature. 46 ml (0.09 mol) of an approximately 12% strength sodium hypochlorite solution are metered in within 20 minutes with vigorous stirring and the mixture is stirred for a further 4 hours during which the reaction temperature rises to 35° C. The reaction mixture is added to 250 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product (28 torr, 65°–70°C.), 9.39 g (72% of theory) of 3-trifluoroacetylpyridine are obtained. $n_D^{20}$: 1.4796.

EXAMPLE 22

2-Phenoxy-4-trifluoroacetylfluorobenzene 14.37 g (0.05 mol) of 2,2,2-trifluoro-1-(4-fluoro-3-phenoxyphenyl)ethanol and 0.85 g (0.0025 mol) of tetrabutylammonium hydrogen sulfate are dissolved in 200 ml of methylene chloride at room temperature. 31 ml (0.06 mol) of an approximately 12% strength sodium hypochlorite solution are metered in within 20 minutes with vigorous stirring and the mixture is stirred for a further 6 hours at room temperature. The reaction mixture is added to 200 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.2 mbar, 150°–165° C. bath temperature), 10.8 g (76% of theory) of 2-phenoxy-4-trifluoroacetylfluorobenzene are obtained. $n_D^{20}$: 1.5230.

EXAMPLE 23

Trifluoroacetylbenzene 10.0 g (0.057 mol) of 2,2,2-trifluoro-1-phenylethanol and 0.96 g (0.0028 mol) of tetrabutylammonium hydrogen sulfate are dissolved in 250 ml of methylene chloride at room temperature. 35 ml (0.068 mol) of an approximately 12% strength sodium hypochlorite solution are metered in within 20 minutes with vigorous stirring and the mixture is stirred for a further 6 hours at room temperature. The reaction mixture is added to 200 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (24 torr, 90°–115° C. bath temperature), 7.45 g (75% of theory) of trifluoroacetylbenzene are obtained. $n_D^{20}$: 1.4658.

EXAMPLE 24

4-Trifluoroacetyltrifluoromethylbenzene 25.4 g (0.1 mol) of 2,2,2-trifluoro-1-(4-trifluoromethylphenyl)ethanol and 1.76 g (0.005 mol) of tetrabutylammonium hydrogen sulfate are dissolved in 350 ml of methylene chloride at room temperature. 108 ml (0.125 mol) of an approximately 12% strength sodium hypochlorite solution are metered in within 20 minutes with vigorous stirring and the mixture is stirred for a further 5 hours at room temperature. The reaction mixture is added to 400 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product (18 torr, 60°–61° C.), 16.74 g (66.5% of theory) of 4-trifluoroacetyltrifluoromethylbenzene are obtained, which, according to GC, is 96.7% pure. $n_D^{20}$: 1.4146.

EXAMPLE 25

Trifluoromethyl cyclohexyl ketone 10.67 g (0.059 mol) of 2,2,2-trifluoro-1-cyclohexylethanol and 0.98 g (0.003 mol) of tetrabutylammonium hydrogen sulfate are dissolved in 250 ml of methylene chloride at room temperature. 37 ml (0.069 mol) of an approximately 12% strength sodium hypochlorite solution are metered in within 20 minutes with vigorous stirring and the mixture is stirred for a further 4 hours during which the reaction temperature rises to 30° C. The reaction mixture is added to 200 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product (28 torr, 80°–82° C.), 4.86 g (46% of theory) of trifluoromethyl cyclohexyl ketone are obtained. $n_D^{20}$: 1.4043.

EXAMPLE 26

6-Phenoxy-2-trifluoroacetylpyridine 9.38 g (0.035 mol) of 2,2,2-trifluoro-1-(6-phenoxy-2-pyridyl)ethanol and 0.58 g (0.0017 mol) of tetrabutylammonium hydrogen sulfate are dissolved in 200 ml of methylene chloride at room temperature. 22 ml (0.042 mol) of an approximately 12% strength sodium hypochlorite solution are metered in within 15 minutes with vigorous stirring and the mixture is stirred for a further 4 hours during which the reaction temperature rises to 30° C. The reaction mixture is added to 200 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (0.4 mbar, 180° C. bath temperature), 4.75 g (50.6% of theory) of 6-phenoxy-2-trifluoroacetylpyridine are obtained. $n_D^{20}$: 1.5298.

EXAMPLE 27

2-Chloro-5-trifluoroacetylpyridine 1.7 g (0.005 mol) of tetrabutylammoninm hydrogen sulfate are added to a mixture of 200 ml of a 0.2M NaBr solution and 21.2 g (0.1 mol) of 2-chloro-5-(2,2,2-trifluoro-1-hydroxyethyl)pyridine, dissolved in 50 ml of ethyl acetate. The aqueous phase is brought to pH 10 with dilute NaOH solution. This mixture is electrolyzed in an undivided cell on a platinum anode and a stainless steel cathode at room temperature and a current density of 30 mA/cm$^2$ up to a current flow of 21 Ah (7.8 F/mol). Monitoring with GC indicates complete reaction the proportion of 2-chloro-5-trifluoroacetylpyridine is 72%. After the electrolysis, the phases are separated and the aqueous phase is neutralized and extracted several times with ethyl acetate. The combined organic phases are dried with sodium sulfate and the volatiles are distilled off. Following distillation of the crude product at 0.3 mbar, 12.8 g (61.1% of theory) of 2-chloro-5-trifluoro-acetylpyridine of boiling point 50°–51° C. are obtained, which, according to GC, is 98.7% pure.

EXAMPLE 28

2-(2,2,2-Trifluoroethoxy)-5-trifluoroacetylpyridine 2.6 g (0.0095 mol) of 2-(2,2,2-trifluoroethoxy)-5-(2,2,2-trifluoro-1-hydroxyethyl)pyridine and 0.18 g (0.0005 mol) of tetrabutylammonium hydrogen sulfate are dissolved in 10 ml of chloroform at room temperature and 1.07 ml of a 48% strength aqueous solution of HBr are added. 4.24 ml (0.041 mol) of a 30% strength solution of H$_2$O$_2$ are slowly added dropwise at about 45° C. with vigorous stirring and the mixture is stirred for a further 24 hours. The reaction mixture is added to 200 ml of water, the phases are separated, the aqueous phase is extracted several times with chloroform and the combined organic phases are washed with 5% strength sodium bicarbonate solution and with water. After drying the organic phase with sodium sulfate, the volatiles are distilled off. Distillation of the crude product in a kugelrohr (25 torr, 100°–200° C. bath temperature) yields 1.65 g (60% of theory) of 2-(2,2,2-trifluoroethoxy)-5-trifluoroacetylpyridine, which, according to GC, is 98.3% pure.

EXAMPLE 29

4-Trifluoroacetyltrifluoromethoxybenzene 24.0 g (0.09 mol) of 2,2,2-trifluoro-1-(4-trifluoromethoxyphenyl)ethanol and 1.57 g (0.0046 mol) of tetrabutylammonium hydrogen sulfate are dissolved in 250 ml of methylene chloride at room temperature. 100 ml (0.12 mol) of an approximately 12% strength sodium hypochlorite solution are metered in within 20 minutes with vigorous stirring and the mixture is stirred for a further 5 hours during which the temperature rises to 40° C. The reaction mixture is added to 400 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (14 torr, bath temperature 100°–115° C.), 17.19 g (74% of theory) of 4-trifluoroacetyltrifluoromethoxybenzene are obtained. $n_D^{20}$: 1.4188.

EXAMPLE 30

4-Trifluoroacetyldifluoromethoxybenzene 23.67 g (0.098 mol) of 2,2,2-trifluoro-1-(4-difluoromethoxyphenyl)ethanol and 1.66 g (0.0049 mol) of tetrabutylammonium hydrogen sulfate are dissolved in 200 ml of methylene chloride at room temperature. 105 ml (0.124 mol) of an approximately 12% strength sodium hypochlorite solution are metered in within 25 minutes with vigorous stirring and the mixture is stirred for a further 5 hours during which the temperature rises to 40° C. The reaction mixture is added to 500 ml of water, the phases are separated, the aqueous phase is extracted several times with methylene chloride and the combined organic phases are washed with saturated aqueous sodium chloride solution. After drying the organic phase with sodium sulfate, the volatiles are distilled off. Following distillation of the crude product in a kugelrohr (15 torr, bath temperature 90°–110° C.), 16.0 g (68% of theory) of 4-trifluoroacetyl-difluoromethoxybenzene are obtained. $n_D^{20}$: 1.4201.

We claim:

1. A process for preparing compounds of the formula I

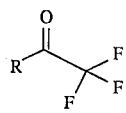

where R is an unsubstituted or substituted aliphatic or aromatic hydrocarbon radical or an unsubstituted or substituted aliphatic or aromatic heterocyclic radical, wherein an alcohol of the formula II

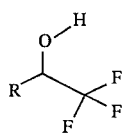

where R has the abovementioned meaning, is reacted in an aprotic solvent in the presence of 0.1–20 mol %, based on the alcohol of the structure II employed, of a phase-transfer catalyst, with a 1–20% strength by weight aqueous solution of compounds of the structure IV or a 1–20% strength by weight aqueous solution of a compound generated in situ of the structure IV $$YO_nH \quad\quad (IV)$$

where Y is =Cl, Br or I and n is =1, or of its salts, at temperatures from 0° C. up to the boiling point of the mixture.

2. The process as claimed in claim 1, wherein a compound of the formula IV or one of its salts is employed as such in the form of the aqueous solution.

3. The process as claimed in claim 1, wherein an aqueous solution of a compound of the formula IV which has been prepared in situ by electrochemical means or by reaction of $H_2O_2$ with a hydrohalic acid or its salts is employed.

4. The process as claimed in claim 1, wherein one or more of the following conditions are fulfilled:
   a) the aprotic solvent is methylene chloride, chloroform, ethyl acetate, toluene, xylene or chlorobenzene,
   b) the phase-transfer catalyst is an ammonium salt of the formula III

where $R^3$–$R^6$ are the same or different and are benzyl, phenyl, ($C_1$–$C_{16}$)-alkyl and $X^-$ is $OH^-$ or anions of monobasic or polybasic acids,
   c) 1–10 mol % of phase-transfer catalyst are added, related to the alcohol II employed,
   d) a 5–15% strength (percent by weight) aqueous solution of a compound of the formula IV or of an alkali metal or alkaline earth metal salt of this compound is used,
   e) 1–2 mol of oxidizing agent of the structure IV are employed per mol of alcohol of the structure II,
   f) the reaction temperature is 0° to 40° C.

5. The process as claimed in claim 1, wherein one or more of the following conditions are fulfilled:
   a) the aprotic solvent is methylene chloride, chloroform, ethyl acetate, toluene, xylene or chlorobenzne,
   b) the phase-transfer catalyst is an ammonium salt of the formula III

where $R^3$–$R^6$ are the same or different and are benzyl, phenyl, ($C_1$–$C_8$)-alkyl and $X^-$ is $Cl^-$, $Br^-$ or $HSO_4^-$,
   c) 1–10 mol % of ammonium salt of the formula III are added as the phase-transfer catalyst,
   d) an aqueous solution of HOCl, $HClO_4$, HOBr, $HBrO_2$, $HBrO_3$, $HIO_4$ or their salts is used as the 5–15% strength aqueous solution of a compound of the structure IV,
   e) 1–2 mol of oxidizing agent of the structure IV are employed per mol of alcohol of the structure II,
   f) the reaction temperature is 0° C. to 40° C.

6. The process as claimed in claim 1, wherein one or more of the following conditions are fulfilled:
   a) the aprotic solvent is methylene chloride, ethyl acetate, toluene, xylene or chlorobenzene,
   b) the phase-transfer catalyst is benzyltrimethylammonium chloride, tetraethylammonium bromide, tetrapropylanunoniumbromide, tetrabutylammonium bromide, tetrabutylammonium hydrogen sulfate, hexadecyltrimethylammonium bromide or benzyltributylammonium bromide, c) 1–10 mol % of ammonium salt of the formula III are added as the phase-transfer catalyst, d) an aqueous solution of HOCl, HOBr, NaOCl, NaOBr or Ca(OCl)$_2$ is used as the 5–15% strength aqueous solution of a compound of the structure IV, e) 1–2 mol of oxidizing agent of the structure IV are employed per mol of alcohol of the structure II, f) the reaction temperature is 0° to 40° C.

7. The process as claimed in claim 1, wherein one or more of the following conditions are fulfilled:

a) the aprotic solvent is methylene chloride, ethyl acetate, toluene, xylene or chlorobenzene, b) the phase-transfer catalyst is tetrabutylammonium bromide or tetrabutylammonium hydrogen sulfate, c) 1–10 mol % of ammonium salt of the formula III are added as the phase-transfer catalyst, d) an aqueous solution of sodium hypobromite, sodium hypochlorite or calcium hypochlorite is used as the 5–15% strength aqueous solution of a compound of the structure IV, e) 1–2 mol of oxidizing agent of the structure IV are employed per mol of alcohol of the structure II, f) the reaction temperature is 0° to 40° C.

8. The process as claimed in claim 1, wherein R in formula II contains, as hydrocarbon radical, 1 to 30 carbon atoms and, a heterocyclic ring having 5- to 6-ring members and 1 to 2 hetero atoms.

9. The process as claimed in claim 1, wherein R in formula II is phenyl, naphthyl, pyridyl, pyrimidyl, pyridazinyl, thiazolyl or imidazolyl, where these radicals are optionally substituted by $C_1$–$C_{12}$-alkyl, phenyl, benzyl, $C_7$–$C_{14}$-alkylphenyl, $C_8$–$C_{14}$-alkylbenzyl, $C_1$–$C_{12}$-alkoxy, phenoxy, benzyloxy, $C_7$–$C_{12}$-alkylphenoxy, $C_8$–$C_{14}$-alkylbenzyloxy, $C_7$–$C_{12}$-phenoxyalkyl, $C_7$–$C_{14}$-alkoxyphenyl, cyclopentyl, cyclohexyl, cyclopropyl, $C_1$–$C_{12}$-haloalkyl, $C_1$–$C_{12}$-haloalkoxy, CN, OH, F, Cl, Br or I, where the aliphatic radicals may be interrupted by O, S, $NR^1$, where $R^1$ is H, C1–C18-alkyl, C1–C18-haloalkyl, C3–C6-cycloalkyl, phenyl, benzyl or pyridyl or by —CO— or —C(O)O—.

10. A process as claimed in claim 1 wherein R is selected from the group consisting of pyridine, thiophene, unsubstituted phenyl, substituted phenyl, and cylohexyl.

11. The process, as claimed in claim 1, consisting essentially of reacting an alcohol of formula II with an aprotic solvent in the presence of 0.1–20 mol %, based on the alcohol of formula II employed, of a phase-transfer catalyst, with a 1–20% strength by weight aqueous solution of compounds of the structure IV or a 1–20% strength by weight aqueous solution of a compound generated in situ of the structure IV, wherein R of formula II is $C_1$–$C_6$-alkyl, $C_3$–$C_6$-cycloalkyl, $C_1$–$C_6$-haloalkyl or unsubstituted or substituted phenyl, benzyl, pyridyl, pyrimidyl, pyridazinyl or thiazolyl, with $C_1$–$C_6$-haloalkyl, $C_1$–$C_6$-haloalkoxy, $C_1$–$C_6$-alkyl and $C_1$–$C_6$-alkoxy being suitable substitutions, and wherein Y of structure IV is Cl, Br or I and n is an integer from 1 to 4, or of its salts, at temperatures from 0° C. up to the boiling point of the mixture.

\* \* \* \* \*